(12) United States Patent
Navran

(10) Patent No.: US 11,744,902 B2
(45) Date of Patent: Sep. 5, 2023

(54) TARGETING TECHNOLOGY TO SELECTIVELY EXPRESS MRNAS IN CARDIOMYOCYTES WHILE AVOIDING STIMULATION OF CARDIAC FIBROBLASTS

(71) Applicant: Animatus Biosciences, Inc., Houston, TX (US)

(72) Inventor: Stephen Navran, Houston, TX (US)

(73) Assignee: Animatus Biosciences, Inc., Houston, TX (US)

( * ) Notice: Subject to any disclaimer, the term of this patent is extended or adjusted under 35 U.S.C. 154(b) by 0 days.

(21) Appl. No.: 17/711,125

(22) Filed: Apr. 1, 2022

(65) Prior Publication Data
US 2022/0323606 A1    Oct. 13, 2022

Related U.S. Application Data

(60) Provisional application No. 63/171,197, filed on Apr. 6, 2021.

(51) Int. Cl.
*A61K 47/69* (2017.01)
*C12N 15/115* (2010.01)
*A61P 9/00* (2006.01)

(52) U.S. Cl.
CPC ............ *A61K 47/6925* (2017.08); *A61P 9/00* (2018.01); *C12N 15/115* (2013.01); *C12N 2310/16* (2013.01); *C12N 2310/3515* (2013.01)

(58) Field of Classification Search
None
See application file for complete search history.

(56) References Cited

U.S. PATENT DOCUMENTS

| | | | | |
|---|---|---|---|---|
| 2014/0206753 A1* | 7/2014 | Guild | ................ | A61P 7/06 |
| | | | | 514/44 R |
| 2015/0160237 A1* | 6/2015 | Wiencierz | .............. | A61K 35/34 |
| | | | | 435/325 |
| 2019/0022645 A1 | 1/2019 | Hu et al. | | |
| 2020/0297814 A1 | 9/2020 | Nikolaev et al. | | |
| 2021/0069294 A1* | 3/2021 | Schwartz | ............... | C12N 15/86 |
| 2021/0187123 A1* | 6/2021 | Schwartz | ........... | C07K 14/4702 |

FOREIGN PATENT DOCUMENTS

| | | | | |
|---|---|---|---|---|
| WO | WO 2015/054253 | | 4/2015 | |
| WO | WO-2016123365 A1 * | | 8/2016 | ......... A61K 47/6911 |
| WO | WO-2019136031 A1 * | | 7/2019 | ......... A61K 38/1709 |
| WO | WO 2019/213257 | | 11/2019 | |

OTHER PUBLICATIONS

Kulkarni et al. Acc, Chem. Res. 52, 2435-2444 (Year: 2019).*
Debets et al. Chem Comm. 46, 97-99 (Year: 2010).*
Eroglu et al. Journal of drug targeting vol. 28, 225-244,, issue 3 (Year: 2020).*
Lee, Kk et al,) Peptide-enhanced mRNA transfection in cultured mouse cardiac fibroblasts and direct reprogramming towards cardiomyocyte-like cells. International Journal of Nanomedicine, vol. 10, Mar. 6, 2015, doi: 10.2147/IJN.S75124, pp. 1841-1854; abstract.
International Search Report PCT US22/22994, pp. 1-8, dated Oct. 13, 2022.

* cited by examiner

*Primary Examiner* — Brian Whiteman
(74) *Attorney, Agent, or Firm* — Eric P. Mirabel, JD, LLM

(57) ABSTRACT

Disclosed is a process of having mRNA selectively adsorbed and expressed in cardiomyocytes, by coupling an aptamer which selectively targets lipid nanoparticles containing the mRNA to cardiomyocytes and does not bind to fibroblasts, to lipid nanoparticles containing the mRNA; and administering the aptamer coupled to the lipid nanoparticles containing the mRNA to a host animal under conditions suitable for expression of the mRNA in cardiomyocytes. One preferred sequence for such an aptamer is: AGC CGTTCTGGGGGGTCGACGTTGCATCGTCA (SEQ ID NO:20), and wherein the mRNA encodes Stemin and/or YAP1(5SA).

19 Claims, 4 Drawing Sheets
(3 of 4 Drawing Sheet(s) Filed in Color)
Specification includes a Sequence Listing.

Ventricular Fibroblasts

Round 4          Round 10

Cardiomyocytes

Round 4          Round 10

TARGETING TECHNOLOGY TO SELECTIVELY EXPRESS MRNAS IN CARDIOMYOCYTES WHILE AVOIDING STIMULATION OF CARDIAC FIBROBLASTS

SEQUENCE LISTING

The instant application contains a Sequence Listing which has been submitted electronically in ASCII format and is hereby incorporated by reference in its entirety. Said ASCII copy, created on Apr. 15, 2022, is named ANIMA-CARDIO (US) and is 32,768 bytes in size.

BACKGROUND

It is well known that activation of cardiac fibroblasts after an injury such as an infarct are primarily responsible for the ensuing fibrosis (Kong P. et al. 2014). Consequently, it is critically important that for any therapeutic, one avoids activating cardiac fibroblasts.

Yes-associated protein (YAP) is a transcription coactivator and a potent growth promoter that is directly phosphorylated by the Hippo pathway kinases Lats1 and Lats2, and then inhibited through cytoplasmic retention and degradation. YAP activation facilitates cell proliferation, evasion from apoptosis, and stem cell self-renewal. Additional studies have indicated that the Hippo pathway is upregulated in heart failure and that a Hippo pathway deficiency reversed systolic heart failure (Leach et al., 2017). Such results have increased interest in the manipulation of the Hippo pathway as an approach to the treatment of heart failure. The transcription co-activator YAP, as a key regulator in the Hippo signaling pathway, has been proposed as a target for manipulation.

Zhao et al. generated an active form of YAP, termed YAP1(5SA) (see mRNA sequence below) by mutating all the LATS1/2 phosphorylation sites from serine to alanine (Zhao et al., 2007). The phosphorylation sites mutation of YAP prevents YAP protein degradation. YAP1(5SA) enters the nucleus and binds with TEAD to regulate nuclear targets. Recently, YAP1(5SA) has been proven to partially reprogram the highly differentiated adult mouse cardiomyocytes to a more primitive proliferative state (Monroe et al., 2019).

SRF is a gene on chromosome 6p21.1 that encodes a transcription factor which binds to the serum response element. A study involving one SRF mutant (SRF-153(A3), referred to herein as Stemin (see sequence below; pdf attached) showed that Stemin inhibited the induction of sarcomere assembly factors involved in cardiomyocyte differentiation thereby blocking the normal SRF-mediated cardiac muscle differentiation program resulting in the production of undifferentiated, proliferative cells. Stemin, or SRF-153(A3), showed a powerful activation of at least 15 stem cell marker genes, such as Rex1, Nanog, October 4, Sox2, Esg1, SFmbt2, Rhox6 and proliferin. Stemin also inhibited the induction of many cardiac myocyte genes such as sarcomeric actins, heavy and light chain myosins, troponins, channels and structural genes. Expression of sarcomeric assembly factors such as Actinin2, Nebulin, Titin, Myomesin, Obscurin Filamin, Smyd1 and SNF1-K2 were blocked. In addition, evidence for Stemin fostering cell replication was shown by the up regulation of cyclins A2, B1, E1 and D1.

Accordingly, delivery of mRNAs encoding YAP1(5SA) or Stemin to cardiomyocytes in a form suitable for expression would be expected to be a useful treatment for heart failure and other heart disease. A suitable delivery and expression protocol for mRNAs encoding YAP1(5SA) or Stemin could also be useful for delivering and expression of other mRNAs, selectively to cardiomyocytes.

SUMMARY

Aptamers that selectively bind to cardiomyocytes and are rapidly internalized, have been developed. The most rapidly endocytosed of these aptamers are conjugated to lipid nanoparticles encapsulating Stemin and YAP1(5SA) mRNAs (or Variant Sequences thereof) to deliver the mRNAs only to cardiomyocytes for expression. To develop aptamers that selectively bind to cardiomyocytes, the Cell-SELEX (Systematic Evolution of Ligands by Exponential enrichment) procedure was used. Nucleic acid-based aptamers are single-stranded DNAs or RNAs able to bind with high affinity and specificity to a given target, usually isolated and purified, by folding in 3D structures. The procedure is based on the isolation of high affinity ligands from a combinatorial single-stranded nucleic acid library through repeated cycles of binding, partitioning, and amplification (Ellington, A. D.; et al. 1999). Following SELEX cycles, the final aptamer pool is subjected to sequencing for the identification of the best binding sequences. A variant of the SELEX procedure, Cell-SELEX, uses living cells as the target (Rahimizadeh K. et al. 2017). Advantages of Cell-SELEX are that the identity of the target, usually a protein, does not need to be known and that the target is in its native conformation. Additionally, herein, the aptamer pool was negatively selected against ventricular fibroblasts to insure that there is no cross-reactivity with fibroblasts.

After 10 rounds of selection of human cardiomyocytes with every other round a negative selection against ventricular fibroblasts, a pool of 96 cardiomyocyte-specific aptamers was produced, having sequences as shown in Table I below. The aptamers which lead to rapid internalization (as needed for expression of the mRNA carried by the lipid nanoparticles) are then determined.

The same preferred aptamers (or aptamer Variant Sequences thereof, defined below) could be used with lipid nanoparticles carrying mRNA encoding other molecules, including cytokines and/or other therapeutic products selectively to cardiomyocytes, as well as mRNA encoding mutants of such cytokines and/or other therapeutic products which remain biologically active; such as mutants with amino acid sequences which only have conservative substitutions such that the molecule has at least 70%, 80%, 90%, 95%, 96%, 97%, 98% or 99% identity to the corresponding wild type sequence listing (hereinafter referred to as "Variant Sequences"). The invention also includes the DNA or nucleic acid sequences encoding the mRNAs, Variant Sequences or aptamer Variant Sequences, as well as vectors incorporating such nucleic acid sequences.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
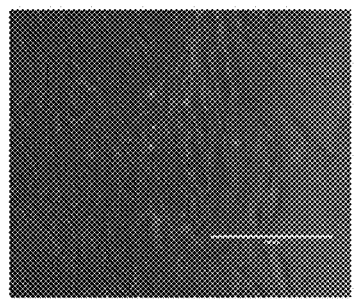
FIG. 1 is an image showing screening results for a selected pool of aptamers displaying binding only to cardiomyocytes; not fibroblasts.
Figure 1:
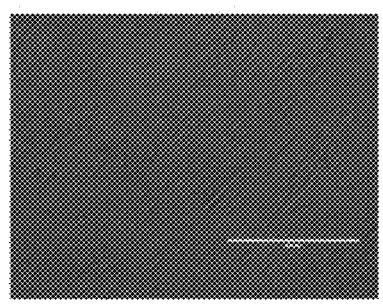
Figure 1:
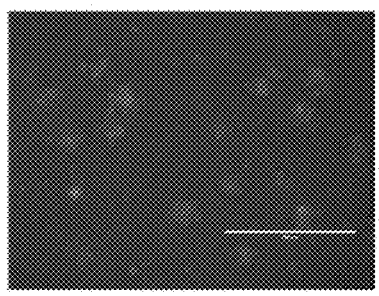
Figure 1:
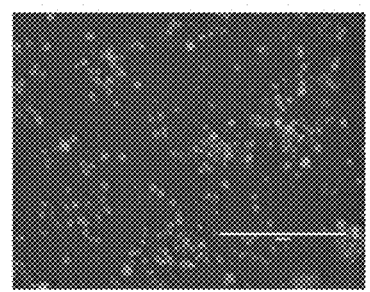

It should be understood that the drawings and the associated descriptions below are intended only to illustrate one or more embodiments of the present invention, and not to limit its scope. The drawings are not necessarily to scale.

DETAILED DESCRIPTION

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

When referring to a gene, "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; or, can be a gene that has one or more point mutations leading to a change in the amino acid of the encoded protein or results in aberrant splicing of the gene transcript.

"Naturally-occurring" or "wild-type" refers to the form found in nature. For example, a naturally occurring or wild-type polypeptide or mRNA sequence is a sequence present in an organism, which has not been intentionally modified by human manipulation.

The terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 units in length (nucleotide bases or amino acids).

FIG. 1 shows an aptamer library of FAM labeled DNA aptamers screened by Cell-SELEX positively against human cardiomyocytes and negatively against human ventricular myocytes. After 10 rounds the selected pool of aptamers displayed binding only to cardiomyocytes; not fibroblasts. The selected pool was sequenced and the aptamers were ranked for frequency counts and stability. The 23 highest ranking aptamers were synthesized for subsequent testing.

In order for a aptamer to be effective in carrying nanoparticle mRNAs into cardiomyocytes, it must not only bind selectively, but also it must be rapidly internalized by cardiomyocytes. To test internalization in the mouse model system a microplate fluorescence assay was used to distinguish internalization from binding (Hernandez L I et al. 2013).

AM-labeled aptamers were incubated with mouse cultured cardiomyocytes for 1 hour in a multi-well plate and then washed with a high salt buffer to remove surface bound aptamer. Fluorescence was recorded for each aptamer and normalized to protein. The results are depicted in FIG. 2, showing internalization of 23 aptamers and a control consisting of an unrelated sequence of the same size.

Figure 2:
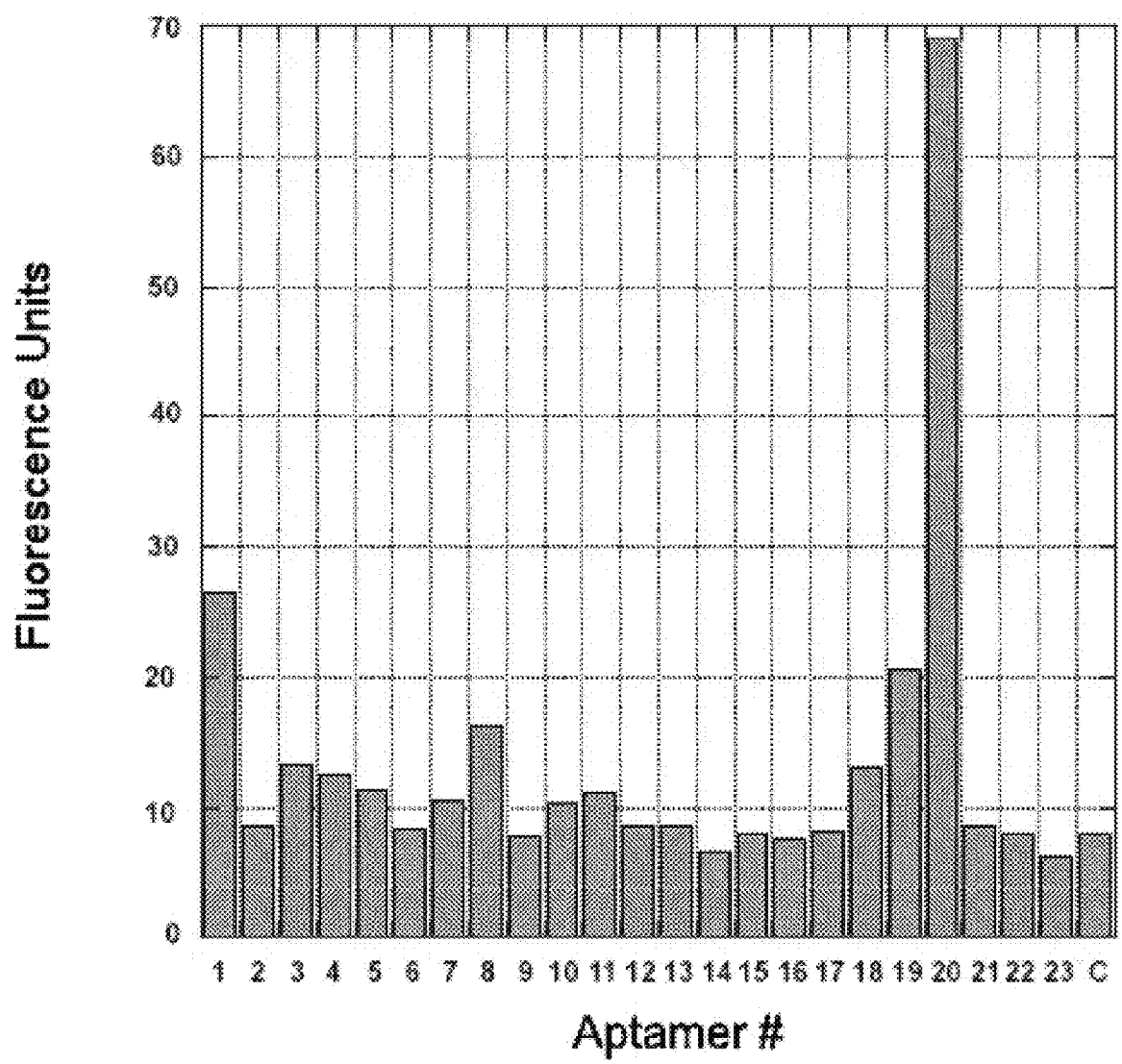
FIG. 2 depicts results from a microplate fluorescence assay used to distinguish aptamer internalization from binding.

As seen in FIG. 2, one aptamer, #20, with a sequence of AGCCGTTCTGGGGGGTCGACGTTGCATCGTCA (SEQ ID NO:20), was taken up significantly more than others. Aptamer Nos. 1 (SEQ ID NO:1) and 19 (SEQ ID NO:19) in Table I also showed high uptake in cardiomyocytes.

This aptamer and Variant Sequences thereof will be coupled to mRNA encapsulated lipid nanoparticles to facilitate selective mRNA targeting to cardiomyocytes. Sequences of other aptamers tested are shown in Table I, and Variant Sequences of any of the following aptamers could also be tested the same way.

TABLE I

| # | Name | Sequence | SEQ ID NO |
|---|------|----------|-----------|
| 1 | Z83A3G | GAGAGAGTCGTGGGGTGGGGCGGGCGGCAGTG | (SEQ ID NO: 1) |
| 2 | AxAS3K | GCCAGATAGTCATGTCAGCGCAAAATCACTTA | (SEQ ID NO: 2) |
| 3 | AxAS4T | GTGTTGCGGCAGAAGTGATGTGAGTTCGTGGG | (SEQ ID NO: 3) |
| 4 | AxAS32 | GGAAGAGGTGGGGAATAGGTTCGGTACATTAA | (SEQ ID NO: 4) |
| 5 | AxASYU | AAATCACGCTGTGTGAAGGTCCTTCTCTCCAA | (SEQ ID NO: 5) |
| 6 | AxAS1S | CCATGATCACATACGCGTACATTACACGAACA | (SEQ ID NO: 6) |
| 7 | AxASZQ | AGGTCAGTGTGTTCGATAGTTCGTGGATGGTA | (SEQ ID NO: 7) |
| 8 | Z8VCHB | ACCTCGCTCTCCCCCCGGCTCCGCGAAATTGA | (SEQ ID NO: 8) |
| 9 | AxAS25 | GACGATCGGATGTTGTTGCAGAAGTTCACTAC | (SEQ ID NO: 9) |
| 10 | AxAS39 | GGGAATGGCGCTCGGTAGTTGTACGTTCTCGG | (SEQ ID NO: 10) |
| 11 | AxAS5E | TATCCCTGGGGTCCGGTCAAACACGTAATAGA | (SEQ ID NO: 11) |
| 12 | AxAS5U | TCTAGCACTCGCGTGTGGACGGTAAACCGTCT | (SEQ ID NO: 12) |
| 13 | AxAS3A | GAGCCAGTGACGTTGAAATACGGTCATGGCGG | (SEQ ID NO: 13) |
| 14 | AxAS5P | TCCGTTCCGATTCTGGGAACGTACAGAATTCA | (SEQ ID NO: 14) |
| 15 | AxASZU | AGTGACGTGCGACGTGCACTGAAGCAAGAGCA | (SEQ ID NO: 15) |
| 16 | AxAS3T | GCGGCGAGGTGATATTACCTCACGGCTGTATT | (SEQ ID NO: 16) |
| 17 | AxAS5Q | TCGAACCAGCAGTAAACGTTACTGTGATGGAC | (SEQ ID NO: 17) |
| 18 | AxAS1C | CAACGTGTGTAATGGATATCCATTACTGGTAT | (SEQ ID NO: 18) |
| 19 | AxAS5F | TATGGCGGACAGGGAGGACCACTCAGTTACAG | (SEQ ID NO: 19) |
| 20 | AxASZJ | AGCCGTTCTGGGGGGTCGACGTTGCATCGTCA | (SEQ ID NO: 20) |
| 21 | AxAS3V | GCGTGATGCGTTTCAACGACTGTAGACGGTGA | (SEQ ID NO: 21) |
| 22 | AxAS5Z | TGCGCGATAGTCGAGAATTGGGTTCTCTCGTC | (SEQ ID NO: 22) |
| 23 | AxAS44 | TACGTCGATAAATCGAGCGGAAAGCATACGCT | (SEQ ID NO: 23) |
| 24 | AxAS4N | GTCGCCGTAGGCATTTGGACGTGGGGAACGTT | (SEQ ID NO: 24) |
| 25 | AxAS6J | TTGGGGCACCCAATTTCCTGGTAGGGACAAAT | (SEQ ID NO: 25) |
| 26 | AxAS56 | TGGCCTAGTCAGGGCGTGCGGCTGTCGGGTTC | (SEQ ID NO: 26) |
| 27 | AxASZT | AGTGAAGTCCGTCATACTCGTGACCAGGACGA | (SEQ ID NO: 27) |
| 28 | AxAS1H | CACGGCCAACTTCGTCCAATTGGCAGTACCCA | (SEQ ID NO: 28) |
| 29 | AxAS24 | GACCTCCAGGATGAGTTTCACGAGAGTACTCG | (SEQ ID NO: 29) |
| 30 | AxAS1T | CCCAGCCGGTTTATTAGGTAGAACCGTAAAGC | (SEQ ID NO: 30) |
| 31 | AxAS5W | TGCAGAGTGGATCGGTTGGGGGTAATGAACCA | (SEQ ID NO: 31) |
| 32 | AxASZ1 | ATCGCATACTCGGTCAGACTTTCCTCGCCGAG | (SEQ ID NO: 32) |
| 33 | AxAS1J | CAGATAGTAGCCTCCCGGGGCCCTATCGATCA | (SEQ ID NO: 33) |
| 34 | AxAS1W | CCCGTCTCCGACGAGCTGAACAAGGGAGCTAT | (SEQ ID NO: 34) |
| 35 | AxAS19 | CGCAAGGGCGAAACGGGACAGATCGATGAGTC | (SEQ ID NO: 35) |
| 36 | AxASZA | ACGCAGCGCCCAGGCTCCGGGAGCTATCCCCT | (SEQ ID NO: 36) |

TABLE I-continued

| | | | |
|---|---|---|---|
| 37 | AxASZK | AGCGGCTCCTGTAGAATAGGTGGGCATCGCTC | (SEQ ID NO: 37) |
| 38 | AxAS3W | GCTACGGGAATGCCCGCACACATGAATTTCGT | (SEQ ID NO: 38) |
| 39 | AxASZB | ACGCCAGGCAGGATGCGGATCAGCATTCCTTT | (SEQ ID NO: 39) |
| 40 | AxAS2Y | CTGTGTGTGGGGTCCGCATCCGTAACATGCGA | (SEQ ID NO: 40) |
| 41 | AxAS2U | CTCGGAACGTTTTGCTGGGGGGCCCAGGTATA | (SEQ ID NO: 41) |
| 42 | AxASYX | AAGGCGAGAAGTAAGTTGAAGGTTCTGGCCGC | (SEQ ID NO: 42) |
| 43 | AxAS3I | GCATCCCACTGCACGGCTAAACAACTTAGCAT | (SEQ ID NO: 43) |
| 44 | AxAS2M | CGTGTAGAACTCATGCGACCGCTGGGTCCATA | (SEQ ID NO: 44) |
| 45 | AxASZN | AGGCTTCAACCCGGCTTTAGCGTGAAAAGCAA | (SEQ ID NO: 45) |
| 46 | AxAS2D | CGGAACGGGCCAGCTGGAAGGCGGGTGCTTCG | (SEQ ID NO: 46) |
| 47 | AxAS1N | CAGTGTGAATGGCGGTTCGTCCGATGAGACGT | (SEQ ID NO: 47) |
| 48 | AxASYT | AAACTCGAGAGCAATCGGCGAACCGTGTACGG | (SEQ ID NO: 48) |
| 49 | AxAS2G | CGGAGGGATATTTACGTCGTTCCGTGGAGTTA | (SEQ ID NO: 49) |
| 50 | AxAS3U | GCGGCTCCGGACCGAGCGGTTCTATGAGGTTC | (SEQ ID NO: 50) |
| 51 | AxAS35 | GGAGTAAAGGCGGAAACAGTCCGTGCACAACT | (SEQ ID NO: 51) |
| 52 | AxASZ9 | ATTTGCGGGAGGCTCACGTGCTCTGGCTCGGT | (SEQ ID NO: 52) |
| 53 | AxAS2B | CGCGGGGTCGCTGTAGACTTACTGGGATATCC | (SEQ ID NO: 53) |
| 54 | AxAS12 | CCTGCAGAGGACCGGTCCAGCGCCTCCCCCAG | (SEQ ID NO: 54) |
| 55 | AxAS2Q | CTAGGAGGGAGCGATCCGCCCATAGTTGGATT | (SEQ ID NO: 55) |
| 56 | AxAS21 | GAAATGCACCGCCTTCTACGGACGGCACAATT | (SEQ ID NO: 56) |
| 57 | AxASZE | ACTGGCATCAAGGCACCCAACTGCAAGGTTGC | (SEQ ID NO: 57) |
| 58 | AxAS31 | GCTGAACGTCACTATGGTGCTGGACCGGCATC | (SEQ ID NO: 58) |
| 59 | AxAS37 | GGCAGATTCCATCTGAATTATTCGACGTAGCG | (SEQ ID NO: 59) |
| 60 | AxAS4Z | TACACATAGCGTTCGTCAAGGTGTGTACGGAC | (SEQ ID NO: 60) |
| 61 | AxAS2W | CTGCAAGCCTCCGCCCTAAAAGTTAAGCGAGG | (SEQ ID NO: 61) |
| 62 | AxASY8 | ACCTTAATGGAAACGTTAGGAGGCAGGCCTAA | (SEQ ID NO: 62) |
| 63 | AxAS5Y | TGCGATACTCCCGATACTCGGTGGCAAAACTT | (SEQ ID NO: 63) |
| 64 | AxASZI | AGCAGGGTTTCCCTTGTTCCGCGCTGAGTGTG | (SEQ ID NO: 64) |
| 65 | AxAS4K | GTCACGTCACAGAGGTGTGGTTTCCAGTATGT | (SEQ ID NO: 65) |
| 66 | AxAS5S | TCGGTTCTGCAACCCGGGCAAGCTGTGGTTCG | (SEQ ID NO: 66) |
| 67 | AxAS6E | TTAGGAGGGACCAGTCTGGTGGCAACTGCTGG | (SEQ ID NO: 67) |
| 68 | AxAS1Y | CCGACCTGTAAATGAATCGGCGCACACCGTAT | (SEQ ID NO: 68) |
| 69 | AxAS2C | CGCGTGGAGAAGGCCCAACCGGCTGGATGGTG | (SEQ ID NO: 69) |
| 70 | AxAS5T | TCTAAGTGTAGCTCCCGGTTTGGGTTTCTTAG | (SEQ ID NO: 70) |
| 71 | AxAS4L | GTCAGTCACGGTTTCAGGGAGCGGACTCGTAT | (SEQ ID NO: 71) |
| 72 | AxAS5V | TCTCGGGTCGCCGCAACGAACCTTACTAACTG | (SEQ ID NO: 72) |
| 73 | AxAS3Z | GCTCTCGGGACCAACTGGTGTGTCGTCTGCCG | (SEQ ID NO: 73) |
| 74 | AxAS6K | TTGGTAAACAAAAGTGTCACCACCTTAGCACT | (SEQ ID NO: 74) |

TABLE I-continued

| 75 | AxASZD | ACTGCGTCAGTGGATTCTTCGGGAATTATTGT | (SEQ ID NO: 75) |
| --- | --- | --- | --- |
| 76 | AxAS11 | CCTCGGCGTCCTCAGTTAACGTGCGACCCCGG | (SEQ ID NO: 76) |
| 77 | AxAS3R | GCGCAAATTCGATGTTTGTCCAAGAGCGAGGG | (SEQ ID NO: 77) |
| 78 | AxAS2L | CGTGGGGTGCCAGTCTTCTTAGGACCATGAGC | (SEQ ID NO: 78) |
| 79 | AxAS5A | TAGTAAGTGTCCGAGGTGAATCCTCAAGGCGA | (SEQ ID NO: 79) |
| 80 | AxASZ4 | ATGCACAGGCAAAGATGGAGCAGTCTTTTTCA | (SEQ ID NO: 80) |
| 81 | AxAS3D | GAGTTATAAGCGACGGCTTAAGATTTTATGCA | (SEQ ID NO: 81) |
| 82 | AxASZS | AGTCGAGGGACCTCACACTAAAGTTCCGACGG | (SEQ ID NO: 82) |
| 83 | AxAS1V | CCCGGTTCAACGTGCAATGGCGAGTACCAAGC | (SEQ ID NO: 83) |
| 84 | AxAS3P | GCGAACAGCTTTCACTAATGATGTATTGCTCG | (SEQ ID NO: 84) |
| 85 | AxAS4F | GGTACGGGGAATTGTGACCGTCTTTGGGCAAA | (SEQ ID NO: 85) |
| 86 | AxAS1Q | CATTGAGAAAGGGTTTCTTCCCAGGCTATTCC | (SEQ ID NO: 86) |
| 87 | AxAS3G | GCAAGAGTCCCCGGATAAACGGCTCAAGAGAA | (SEQ ID NO: 87) |
| 88 | AxAS22 | GACATGACCCATCCGGAATGTCTAACGTAATT | (SEQ ID NO: 88) |
| 89 | AxAS3X | GCTACGTCAAATCATGGGACTGTCGTACGCAG | (SEQ ID NO: 89) |
| 90 | AxAS2K | CGGTGGGCGTCGATCCCTGGCTTGTGTGAAGT | (SEQ ID NO: 90) |
| 91 | AxAS4A | GGGGACAAACTACCGGCTTATGCTATGTCTCC | (SEQ ID NO: 91) |
| 92 | AxAS4X | TAAGCGCCATTATGGATCTCTTTGGGAGTGGG | (SEQ ID NO: 92) |
| 93 | AxAS6B | TGTATTCTGCTATGTCGGTGCGTCCGTTGGCT | (SEQ ID NO: 93) |
| 94 | AxASZ5 | ATGCCCCACCGAGCCTAATACGGTATATGTTA | (SEQ ID NO: 94) |
| 95 | AxAS1D | CAAGGACGGAAGAACCGGCGACCTCAATTCAT | (SEQ ID NO: 95) |
| 96 | AxAS4Q | GTGCGATCTTCAATCCCAGGCCGGCGTGGGTC | (SEQ ID NO: 96) |

Figure 3A:
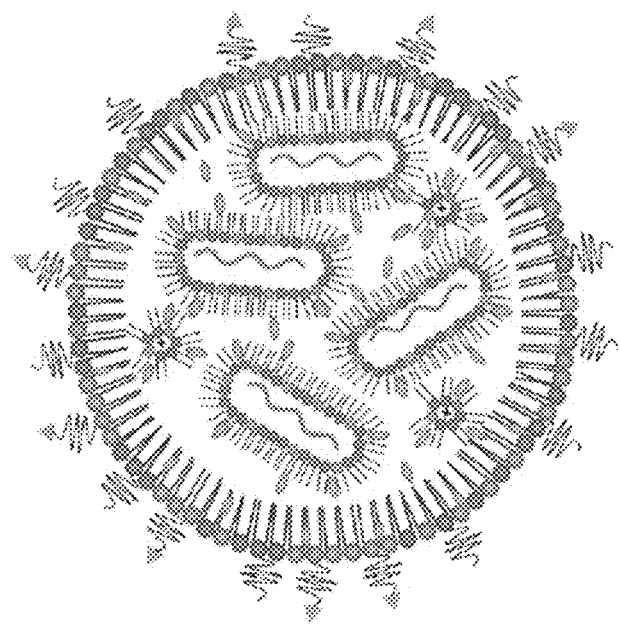
FIG. 3A depicts a LNP with encapsulated mRNA (orange) and DBCO-PEG lipid incorporated on the surface of the nanoparticle.

One approach to determine if mRNAs expressing Stemin and YAP1(5SA) can be taken up and expressed in cardiomyocytes, is to model mRNA uptake as follows. Exemplary mRNAs, preferably encoding luciferase, will be encapsulated into lipid nanoparticles (LNPs) using the NanoAssemblr Platform (Precision NanoSystems, Vancouver, BC) and covalently coupled with the cardiomyocyte targeted aptamer number 20 using a Cu-free click reaction. The aptamer-coupled LNPs containing luciferase mRNA will be tested to determine cellular uptake, through luciferase expression, in mouse hearts. The luciferase expression system can also be used to initially determine the optimal aptamers, followed by luciferase expression testing in animals for further in vivo optimization. The mRNAs complexed with cationic lipids are neutral under physiological conditions and positively charged at acidic pH to enable efficient entrapment of mRNAs. When internalized, the low endosomal pH allows for protonation of the ionizable lipid, destabilization of the endosome and escape of the mRNA into the cytoplasm (Kulkarni J A et al. 2019). FIG. 3A.

Approximately 2% of the surface polyethylene glycol (PEG) of the LNP will be replaced with a modified PEG containing a dibenzylcyclooctyne (DBCO) moiety, preferably having the formula:

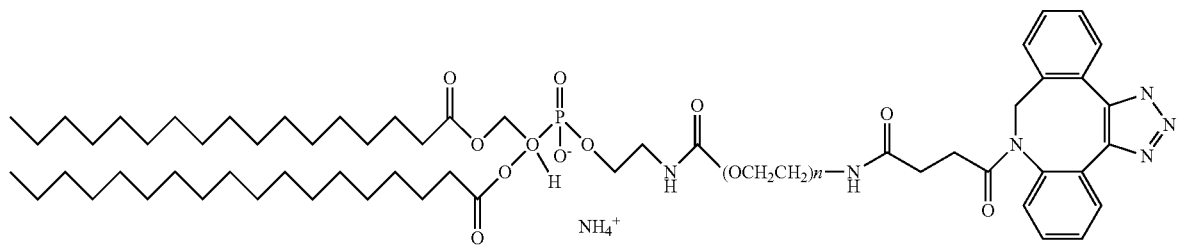

Figure 3B:
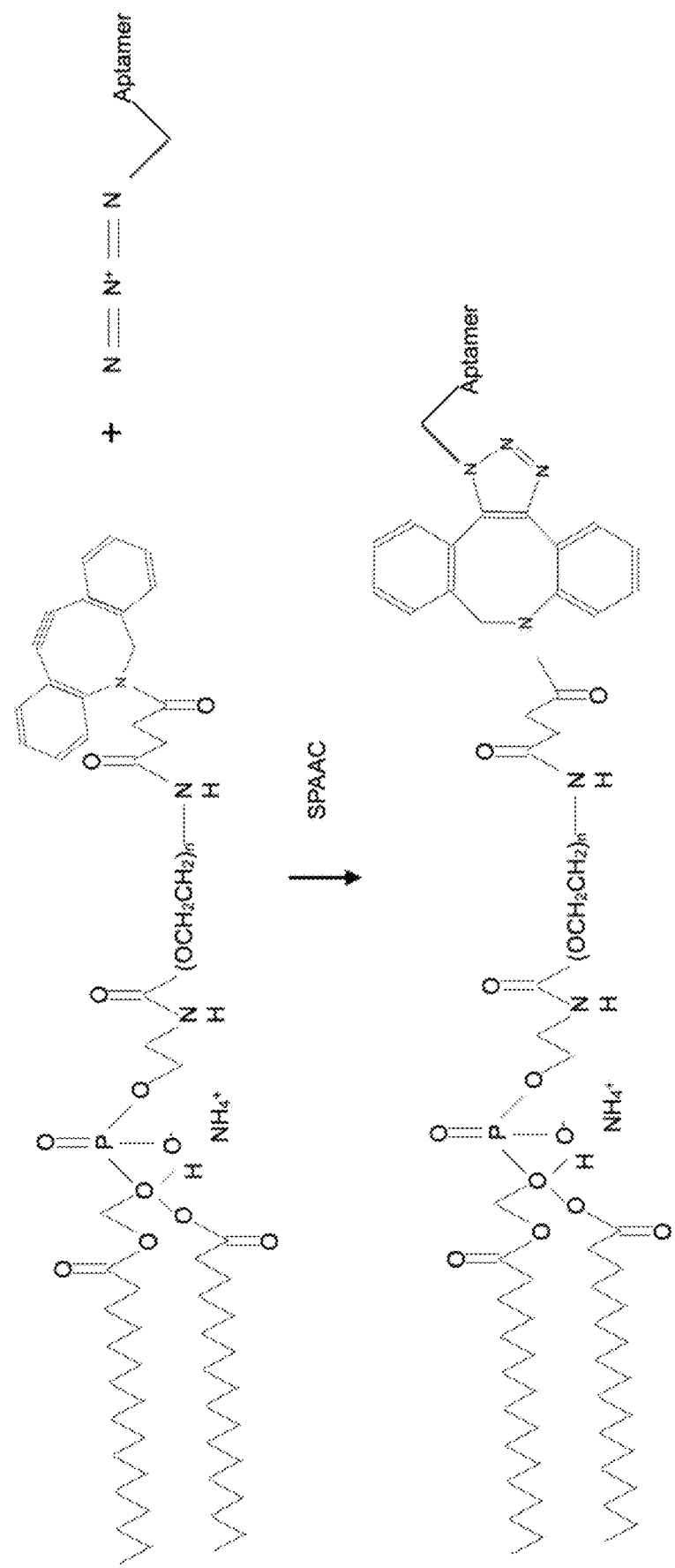
FIG. 3B depicts an azide-functionalized aptamer to allow a Strain-Promoted Azide-Alkyne Click (SPAAC) reaction under mild conditions.

The aptamer will be functionalized with an azide at the 3' or 5' ends to test which orientation of the aptamer produces the most luciferase expression. The DBCO-azide reaction combines high reactivity and adequate hydrophilicity to allow a rapid and complete Strain-Promoted Azide-Alkyne Click (SPAAC) reaction under mild conditions, at neutral pH in aqueous solution (Debets M F et al. 2010). FIG. 3B.

Formulations

After preparation of a suitable functionalized LNP, it can be prepared in a formulation for administration to a subject. A lyophilized formulation is preferred, which as a first step, requires preparing a pre-lyophilized formulation. The amount of mRNA in the pre-lyophilized formulation is determined taking into account the desired dose volumes, mode(s) of administration, etc. The preferred buffer is histidine as it can have lyoprotective properties. Succinate is also a useful buffer.

A lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic, as preferred, though hypertonic reconstituted formulations may also be suitable. In addition, the amount of lyoprotectant must not be too low such that an unacceptable amount of degradation/aggregation of the protein occurs upon lyophilization.

It may be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the LNP and minimizes the formation of particulates after reconstitution.

A mixture of the lyoprotectant (such as sucrose or trehalose) and a bulking agent (e.g. mannitol or glycine) may be used in the preparation of the pre-lyophilization formulation. The bulking agent may allow for the production of a uniform lyophilized cake without excessive pockets therein.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable, so as to retain its physical and chemical stability and integrity upon storage. Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, at about 120° C. for about 30 minutes.

After the LLNP, lyoprotectant and other optional components are mixed together, the formulation is lyophilized. Many different freeze-dryers are available for this purpose such as Hu1150® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation.

Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hours). A secondary drying stage may be carried out at about 0-40° C., depending primarily on the type and size of container and the type of LNP employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the formulation in the container in which reconstitution is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer it to the patient, the lyophilized formulation may be reconstituted with a diluent such that the LNP concentration in the reconstituted formulation is preferably similar to that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and LNP. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Alternatively, a non-lyophilized formulation may be used, including any of the well-known carriers, excipients, buffers, stabilizers, preservatives, adjuvants and other additives described herein and well known in the art.

Dosages and Administration

The formulation described above can be administered to a subject (e.g., a human) in need of the treatment via a suitable route, such as administration by intravenous, intramuscular, intraperitoneal, intracerebrospinal, subcutaneous, intracutaneous, intraarticular, intrasynovial, intrathecal, intradermal, intratumoral, intranodal, intramedulla, oral, inhalation or topical routes; or it may be administered orally, by inhalation spray, topically, rectally, nasally, buccally, vaginally or via an implanted reservoir; and in any case, as a bolus or by continuous infusion over a period of time; or via injectable depot routes of administration such as using 1-, 3-, or 6-month depot injectable or biodegradable materials and methods.

Commercially available nebulizers for liquid formulations, including jet nebulizers and ultrasonic nebulizers are useful for administration. Liquid formulations can be directly nebulized and lyophilized powder can be nebulized after reconstitution. Alternatively, LNP can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats.

An "effective amount" refers to the amount of active agent required to confer therapeutic effect on the subject, either alone or in combination with one or more other active agents. Effective amounts vary, depending on the particular condition being treated, the severity of the condition, the individual patient parameters including age, physical condition, size, gender and weight, the duration of the treatment, the nature of concurrent therapy (if any), the specific route of administration and like factors, all of which are well known to those of ordinary skill in the art and can be addressed with no more than routine experimentation. It is generally preferred that a maximum dose of the individual components or combinations thereof be used, that is, the highest safe dose according to sound medical judgment. A lower dose or tolerable dose for medical reasons, psychological reasons or other reasons, is also appropriate.

Empirical considerations, such as the mRNA half-life, generally will contribute to the determination of the dosage. Frequency of administration may be determined and adjusted over the course of therapy, and is generally, but not necessarily, based on treatment of the condition. Alternatively, sustained continuous release formulations of antibody may be appropriate. Various formulations and devices for achieving sustained release are known in the art.

In one example, dosages may be determined empirically in individuals who have been given one or more administration(s) of the LNP. Individuals are given incremental dosages of the LNP. To assess efficacy, an indicator of the disease can be followed according to routine practice.

Generally, for administration, an initial candidate dosage can be extrapolated from the experiments. For repeated administrations over several days or longer, depending on the condition, the treatment is sustained until a desired suppression of symptoms occurs or until sufficient therapeutic levels are achieved. An exemplary dosing regimen comprises administering an initial higher dose, followed by a lower maintenance dose. However, other dosage regimens may be useful, depending on the pattern of pharmacokinetic decay that the practitioner wishes to achieve. For example, dosing from one-four times a week is contemplated. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen can vary over time.

Conventional methods, known to those of ordinary skill in the art of medicine, can be used to administer the pharmaceutical composition to the subject, depending upon the treatment goal.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like).

For intravenous injection, a pharmaceutical formulation containing the antibody and a physiologically acceptable excipients can be infused. Physiologically acceptable excipients may include, for example, 5% dextrose, 0.9% saline, Ringer's solution or other suitable excipients.

Intramuscular preparations, e.g., a sterile formulation can be dissolved and administered in a pharmaceutical excipient such as Water-for-Injection, 0.9% saline, or 5% glucose solution.

In one embodiment, the LNP is administered via site-specific or targeted local delivery techniques. Examples of site-specific or targeted local delivery techniques include various implantable depot sources of the mRNA or local delivery catheters, such as infusion catheters, an indwelling catheter, or a needle catheter, synthetic grafts, adventitial wraps, shunts and stents or other implantable devices, site specific carriers, direct injection, or direct application. See, e.g., WO 00/53211 and U.S. Pat. No. 5,981,568.

In another embodiment of the present disclosure, an article of manufacture is provided which contains any of the pharmaceutical compositions and formulations described herein and provides instructions for its use and/or reconstitution. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the formulation and the label on, or associated with, the container may indicate directions for reconstitution and/or use. For example, the label may indicate that the formulation is reconstituted to particular concentrations. The container holding the formulation may be a multi-use vial, which allows for repeat administrations (e.g., from 2-6 administrations) of the reconstituted formulation. The article of manufacture may further comprise a second container comprising a suitable diluent (e.g. BWFI). Upon mixing of the diluent and the lyophilized formulation, the final concentration in the reconstituted formulation will generally be set at a threshold. The article of manufacture may further include other materials desirable from a commercial and user standpoint, including other buffers, diluents, filters, needles, syringes, and package inserts with instructions for use.

Example: Testing of mRNA expression from targeted nanoparticles in mouse hearts. In order to verify whether the aptamer-conjugated nanoparticles can bind, enter and express the mRNA contents in a live animal the construct containing luciferase mRNA will be injected into mouse hearts.

Study design: C57BL/6J mice will be injected using microCT imaging to locate the left ventricle with luciferase mRNA encapsulated in lipid nanoparticles conjugated with aptamer #20. Two nanoparticle preparations will be tested, one with the aptamer conjugated at the 5' end and one conjugated at the 3' end. A total of 100 µg of luciferase mRNA will be administered in 3 separate injections of 20 µl. After 24 hours, 150 mg/kg of D-luciferin will be injected subcutaneously 10 minutes prior to imaging the luciferase signal using an IVIS Bioimager. Detection of a luciferase signal will confirm that the lipid nanoparticle mRNA was able to enter ventricular cells, but it does not prove that the aptamer was able to produce luciferase expression selectively in cardiomyocytes. In order to test specificity, the animals will be sacrificed and the left ventricles removed and fixed with paraformaldehyde. The fixed tissue will be sectioned and stained with luciferase and anti-troponin T antibodies. If luciferase and troponin T staining co-localizes, it will indicate that the aptamer conjugated lipid nanoparticles are selective for cardiomyocytes.

A similar protocol using the aptamer-coupled lipid nanoparticles carrying mRNA for Stemin and YAP1(5SA) could be used therapeutically for treating heart disease or heart failure. The Stemin sequence is SEQ No. 97 (same as SEQ ID NO: 2 in U.S. Pat. No. 11,179,479 (incorporated by reference; US Publ'n No. 20210069294A1 is also incorporated by reference)). The mRNA sequence for YAP1(5SA) is shown below as SEQ ID NO: 98.

```
                                                          SEQ ID NO: 98
auggaucccg ggcagcagcc gccgccucaa ccggcccccc agggccaagg gcagccgccu     60
ucgcagcccc cgcaggggca gggcccgccg uccggacccg ggcaaccggc acccgcggcg    120
acccaggcgg cgccgcaggc accccccgcc gggcaucaga ucgugcacgu ccgcggggac    180
ucggagaccg accuggaggc gcucuucaac gccgucauga acccaagac ggccaacgug     240 ccccagaccg ugcccaugag gcuccggaag cugcccguau cccuucuuca agccgccgga    300
gcccaaaucc cacucccgac aggccaguac ugaugcaggc acugcaggag cccugacucc    360
cagcauguuc gagcucauuc cucuccagcu ucucugcagu ugggagcugu uucuccuggg    420
auggaucccg ggcagcagcc gccgccucaa ccggcccccc agggccaagg gcagccgccu    480
ucgcagcccc cgcaggggca gggcccgccg uccggacccg ggcaaccggc acccgcggcg    540
acacugaccc ccacuggagu agucucuggc ccagcagcua cacccacagc ucagcaucuu    600
cgacagucuu cuuuugagaa uaccugauga uguaccucug ccagcgguug ggagauggca    660
aagacaucuu cuggucagag auacuucuua aaucacaucg aucagacaac aacauggcag    720
gaccccagga aggccaugcu gucccagaug aacgucacag ccccaccag uccaccagug     780 cagcagaaua ugaugaacuc ggcuucaggu ccucuuccug auggauggga acaagccaug    840
acucaggaug gagaaauuua cuauauaaac cauaagaaca agaccaccuc uuggcuagac    900
ccaaggcuug acccucguuu ugccaugaac cagagaauca gucagagugc uccagugaaa    960
cagccaccac cccuggcucc ccagagccca cagggaggcg ucaugggugg cagcaacucc   1020
aaccagcagc aacagaugcg acugcagcaa cugcagaugg agaaggagag gcugcggcug   1080
aaacagcaag aacugcuucg gcaggcaaug cggaauauca aucccagcac agcaaauucu   1140
ccaaaauguc aggaguuagc ccugcguagc caguuaccaa cacuggagca ggaugguggg   1200
acucaaaauc cagugucuuc ucccggaau ucucaggaau ugagaacaau gacgaccaau    1260
agcucagauc cuuuccuuaa cagugggcacc uaucacucuc gagaugagag uacagacagu   1320
gggacuaagc augagcagcu acagugucc ucgaacccca gaugacuucc ugaacagugu    1380
ggaugagaug gauacaggug auacuaucaa ccaaagcacc cugcccucac agcagaaccg    1440
uuucccagac uaccuugaag ccauuccugg gacaaaugug gaccuuggaa cacuggaagg    1500
agauggaaug aacauagaag gagaggagcu gaugccaagu cugcaggaag cuugaguuc    1560 ugacauccuu aaugacaugg agucuguuuu ggcugccacc aagcuagaua aagaaagcuu    1620
ucuuacaugg uuauag                                                   1636
```

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", "containing", "having" and "have" are to be read as synonyms and expansively and without limitation. The methods and processes illustratively described herein suitably may be practiced in differing orders of steps, and that they are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

Leach J P, Heallen T, Zhang M, Rahmani M, Morikawa Y, Hill M C, Segura A, Willerson J T, Martin J F. Hippo pathway deficiency reverses systolic heart failure after infarction. Nature. 2017 Oct. 4. doi: 10.1038/nature24045.

Zhao, B., Wei, X., Li, W., Udan, R. S., Yang, Q., Kim, J., Xie, J., Ikenoue, T., Yu, 15 J., Li, L., et al. Inactivation of YAP oncoprotein by the Hippo pathway is involved in cell contact inhibition and tissue growth control. 2007; 21: 2747-2761.

Monroe, Tanner O., Hill, Matthew C., Morikawa, Y., Leach, John P., Heallen, Todd, Cao, Shuyi, Krijger, Peter H. L., Laat, Wouter de, Wehrens, Xander H. T., Rodney, George G., Martin, James F. YAP partially reprograms chromatin accessibility to directly induce adult cardiogenesis in vivo. Dev. Cell 2019; 48:765-779.

Kong P, Christia P, Frangogiannis N G. The pathogenesis of cardiac fibrosis. Cell Mol Life Sci. 2014; 71:549-74

Ellington, A. D.; Szostak, J. W. In vitro selection of RNA molecules that bind specific ligands. Nature 1990; 346: 818-822.

Rahimizadeh K, Al Shamaileh H, Fratini M, Chakravarthy M, Stephen M, Shigdar S and Veedu R N. Development of Cell-Specific Aptamers: Recent Advances and Insight into the Selection Procedures. Molecules 2017: 22: 2070

Hernandez L I, Flenker K S, Hernandez F J, Klingelhutz A J, McNamera J O II, Giangrande P H. Methods for Evaluating Cell-Specific, Cell-internalizing RNA Aptamers. Pharmaceuticals (Basel) 2013; 6:295-319.

Debets M F, van Berkel S S, Schoffelen S, Rutjes F P, van Hest J C, van Delft F L. Azadibenzocyclooctynes for fast and efficient enzyme PEGylation via copper-free (3+2) cycloaddition. Chem Commun (Camb). 2010; 46:97-9.

Kulkarni J A, Witzigmann D, Chen S, Cullis P R, van der Meel R. Lipid Nanoparticle Technology for Clinical Translation of siRNA Therapeutics. Acc Chem Res. 2019; 52:2435-2444.

What is claimed is:

1. A process of having mRNA selectively adsorbed and expressed in cardiomyocytes, comprising:
coupling an aptamer which selectively targets lipid nanoparticles containing the mRNA to cardiomyocytes and does not bind to fibroblasts, to lipid nanoparticles containing the mRNA, wherein the aptamer has one of the following sequences:
GAGAGAGTCGTGGGGTGGGGCGGGCGGCAGTG (SEQ ID NO:1);
TATGGCGGACAGGGAGGACCACTCAGTTACAG (SEQ ID NO:19); and
AGCCGTTCTGGGGGGTCGACGTTGCATCGTCA (SEQ ID NO: 20); and
administering the aptamer coupled to the lipid nanoparticles containing the mRNA to a host animal under conditions suitable for expression of the mRNA.

2. The process of claim 1 wherein the mRNA encodes Stemin or a biologically active variant thereof.

3. The process of claim 1 wherein the mRNA encodes luciferase, or a therapeutic molecule.

4. The process of claim 1 wherein the lipid nanoparticles are covalently coupled with the aptamer using a Cu-free click reaction.

5. The process of claim 1 wherein the lipid nanoparticles have surface polyethylene glycol, and some of the surface polyethylene glycol is replaced with a modified polyethylene glycol containing a dibenzylcyclooctyne moiety.

6. The process of claim 5 wherein the dibenzylcyclooctyne moiety has the formula:

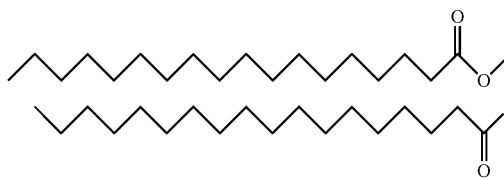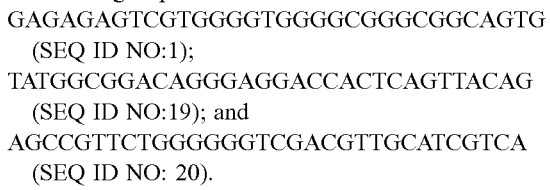

7. The process of claim 5 wherein the dibenzylcyclooctyne moiety reacts with azide in the Cu-free click reaction, and wherein the azide is conjugated to the aptamer.

8. The process of claim 7 wherein either the 3' end or the 5' end of the aptamer is conjugated to the azide.

9. The process of claim 1 wherein before uptake by the lipid nanoparticles, the mRNA is complexed with cationic lipids which are neutral under physiological conditions and positively charged at acidic pH.

10. The method of any of claims 1 to 9 wherein the host animal is a human being.

11. A conjugate for carrying mRNA to be selectively adsorbed and expressed in cardiomyocytes, comprising:
an aptamer which selectively targets lipid nanoparticles containing the mRNA to cardiomyocytes and does not bind to fibroblasts, coupled to lipid nanoparticles containing the mRNA, wherein the aptamer has one of the following sequences:
GAGAGAGTCGTGGGGTGGGGCGGGCGGCAGTG (SEQ ID NO:1);
TATGGCGGACAGGGAGGACCACTCAGTTACAG (SEQ ID NO:19); and
AGCCGTTCTGGGGGGTCGACGTTGCATCGTCA (SEQ ID NO: 20).

12. The conjugate of claim 11 wherein the mRNA encodes Stemin or a biologically active variant thereof.

13. The conjugate of claim 11 wherein the mRNA encodes a therapeutic molecule.

14. The conjugate of claim 11 wherein the lipid nanoparticles are covalently coupled with the aptamer using a Cu-free click reaction.

15. The conjugate of claim 14 wherein a dibenzylcyclooctyne moiety reacts with azide in the Cu-free click reaction, and wherein the azide is conjugated to the aptamer.

16. The conjugate of claim 15 wherein either the 3' end or the 5' end of the aptamer is conjugated to the azide.

17. The conjugate of claim 11 wherein the lipid nanoparticles have surface polyethylene glycol, and some of the surface polyethylene glycol is replaced with a modified polyethylene glycol containing a dibenzylcyclooctyne moiety.

18. The conjugate of claim 17 wherein the dibenzylcyclooctyne moiety has the formula:

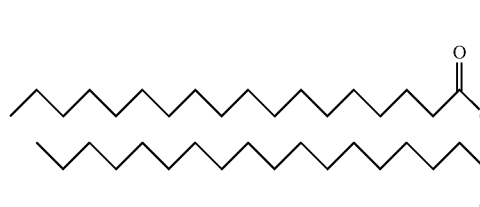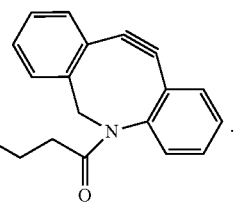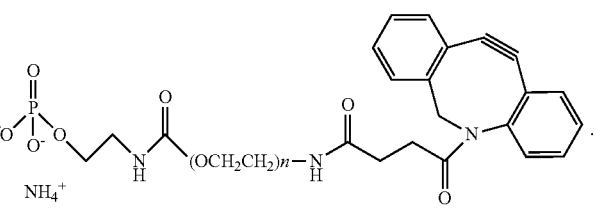

19. The conjugate of claim 11 wherein before uptake by the lipid nanoparticles, the mRNA is complexed with cationic lipids which are neutral under physiological conditions and positively charged at acidic pH.

* * * * *

SEQUENCE LISTING

<160> NUMBER OF SEQ ID NOS: 98

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gagagagtcg tggggtgggg cgggcggcag tg                                     32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gccagatagt catgtcagcg caaaatcact ta                                  32

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtgttgcggc agaagtgatg tgagttcgtg gg                                  32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggaagaggtg gggaataggt tcggtacatt aa                                  32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaatcacgct gtgtgaaggt ccttctctcc aa                                  32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccatgatcac atacgcgtac attacacgaa ca                                  32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aggtcagtgt gttcgatagt tcgtggatgg ta                                  32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 8
acctcgctct cccccggct ccgcgaaatt ga                                    32

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gacgatcgga tgttgttgca gaagttcact ac                                   32

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggaatggcg ctcggtagtt gtacgttctc gg                                   32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tatccctggg gtccggtcaa acacgtaata ga                                   32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tctagcactc gcgtgtggac ggtaaaccgt ct                                   32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gagccagtga cgttgaaata cggtcatggc gg                                   32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 14
tccgttccga ttctgggaac gtacagaatt ca					32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agtgacgtgc gacgtgcact gaagcaagag ca					32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcggcgaggt gatattacct cacggctgta tt					32

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcgaaccagc agtaaacgtt actgtgatgg ac					32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caacgtgtgt aatggatatc cattactggt at					32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tatggcggac agggaggacc actcagttac ag					32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agccgttctg gggggtcgac gttgcatcgt ca                                    32

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcgtgatgcg tttcaacgac tgtagacggt ga                                    32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgcgcgatag tcgagaattg ggttctctcg tc                                    32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tacgtcgata aatcgagcgg aaagcatacg ct                                    32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtcgccgtag gcatttggac gtggggaacg tt                                    32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttggggcacc caatttcctg gtagggacaa at                                    32

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 26
tggcctagtc agggcgtgcg gctgtcgggt tc                                   32

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agtgaagtcc gtcatactcg tgaccaggac ga                                   32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cacggccaac ttcgtccaat tggcagtacc ca                                   32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gacctccagg atgagtttca cgagagtact cg                                   32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cccagccggt ttattaggta gaaccgtaaa gc                                   32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgcagagtgg atcggttggg ggtaatgaac ca                                   32

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 32
atcgcatact cggtcagact ttcctcgccg ag                                32

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cagatagtag cctcccgggg ccctatcgat ca                                32

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cccgtctccg acgagctgaa caagggagct at                                32

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cgcaagggcg aaacgggaca gatcgatgag tc                                32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
acgcagcgcc caggctccgg gagctatccc ct                                32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agcggctcct gtagaatagg tgggcatcgc tc                                32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gctacgggaa tgcccgcaca catgaatttc gt                                         32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acgccaggca ggatgcggat cagcattcct tt                                         32

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctgtgtgtgg ggtccgcatc cgtaacatgc ga                                         32

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctcggaacgt tttgctgggg ggcccaggta ta                                         32

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaggcgagaa gtaagttgaa ggttctggcc gc                                         32

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gcatcccact gcacggctaa acaacttagc at                                         32

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgtgtagaac tcatgcgacc gctgggtcca ta                           32

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aggcttcaac ccggctttag cgtgaaaagc aa                           32

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cggaacgggc cagctggaag gcgggtgctt cg                           32

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cagtgtgaat ggcggttcgt ccgatgagac gt                           32

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaactcgaga gcaatcggcg aaccgtgtac gg                           32

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cggagggata tttacgtcgt tccgtggagt ta                           32

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gcggctccgg accgagcggt tctatgaggt tc                32

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggagtaaagg cggaaacagt ccgtgcacaa ct                32

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atttgcggga ggctcacgtg ctctggctcg gt                32

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cgcggggtcg ctgtagactt actgggatat cc                32

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cctgcagagg accggtccag cgcctccccc ag                32

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctaggaggga gcgatccgcc catagttgga tt                32

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gaaatgcacc gccttctacg gacggcacaa tt                                32

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
actggcatca aggcacccaa ctgcaaggtt gc                                32

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gctgaacgtc actatggtgc tggaccggca tc                                32

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggcagattcc atctgaatta ttcgacgtag cg                                32

<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tacacatagc gttcgtcaag gtgtgtacgg ac                                32

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctgcaagcct ccgccctaaa agttaagcga gg                                32

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
accttaatgg aaacgttagg aggcaggcct aa    32

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgcgatactc ccgatactcg gtggcaaaac tt    32

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agcagggttt cccttgttcc gcgctgagtg tg    32

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gtcacgtcac agaggtgtgg tttccagtat gt    32

<210> SEQ ID NO 66
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcggttctgc aacccgggca agctgtggtt cg    32

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttaggaggga ccagtctggt ggcaactgct gg    32

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccgacctgta aatgaatcgg cgcacaccgt at          32

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cgcgtggaga aggcccaacc ggctggatgg tg          32

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tctaagtgta gctcccggtt tgggtttctt ag          32

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtcagtcacg gtttcaggga gcggactcgt at          32

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tctcgggtcg ccgcaacgaa ccttactaac tg          32

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gctctcggga ccaactggtg tgtcgtctgc cg          32

<210> SEQ ID NO 74
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ttggtaaaca aaagtgtcac caccttagca ct                                    32

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
actgcgtcag tggattcttc gggaattatt gt                                    32

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cctcggcgtc ctcagttaac gtgcgacccc gg                                    32

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcgcaaattc gatgtttgtc caagagcgag gg                                    32

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cgtggggtgc cagtcttctt aggaccatga gc                                    32

<210> SEQ ID NO 79
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tagtaagtgt ccgaggtgaa tcctcaaggc ga                                    32

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
atgcacaggc aaagatggag cagtcttttt ca                                32

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gagttataag cgacggctta agattttatg ca                                32

<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agtcgaggga cctcacacta aagttccgac gg                                32

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cccggttcaa cgtgcaatgg cgagtaccaa gc                                32

<210> SEQ ID NO 84
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gcgaacagct ttcactaatg atgtattgct cg                                32

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ggtacgggga attgtgaccg tctttgggca aa                                32

<210> SEQ ID NO 86
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 86
cattgagaaa gggtttcttc ccaggctatt cc                32

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcaagagtcc ccggataaac ggctcaagag aa                32

<210> SEQ ID NO 88
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gacatgaccc atccggaatg tctaacgtaa tt                32

<210> SEQ ID NO 89
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gctacgtcaa atcatgggac tgtcgtacgc ag                32

<210> SEQ ID NO 90
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cggtgggcgt cgatccctgg cttgtgtgaa gt                32

<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggggacaaac taccggctta tgctatgtct cc                32

<210> SEQ ID NO 92
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
taagcgccat tatggatctc tttgggagtg gg                                        32

<210> SEQ ID NO 93
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgtattctgc tatgtcggtg cgtccgttgg ct                                        32

<210> SEQ ID NO 94
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
atgccccacc gagcctaata cggtatatgt ta                                        32

<210> SEQ ID NO 95
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
caaggacgga agaaccggcg acctcaattc at                                        32

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gtgcgatctt caatcccagg ccggcgtggg tc                                        32

<210> SEQ ID NO 97
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Leu Pro Thr Gln Ala Gly Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Arg Val Pro Gly Asn Gly
        35                  40                  45

Ala Gly Leu Gly Pro Gly Arg Leu Glu Arg Glu Ala Ala Ala Ala
    50                  55                  60

```
Ala Thr Thr Pro Ala Pro Thr Ala Gly Ala Leu Tyr Ser Gly Ser Glu
 65                  70                  75                  80

Gly Asp Ser Glu Ser Gly Glu Glu Glu Leu Gly Ala Glu Arg Arg
                 85                  90                  95

Gly Leu Lys Arg Ser Leu Ser Glu Met Glu Ile Gly Met Val Val Gly
                100                 105                 110

Gly Pro Glu Ala Ser Ala Ala Ala Thr Gly Gly Tyr Gly Pro Val Ser
                115                 120                 125

Gly Ala Val Ser Gly Ala Lys Pro Gly Lys Lys Thr Arg Gly Arg Val
                130                 135                 140

Lys Ile Lys Met Glu Phe Ile Asp Ala Ala Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
                180                 185                 190

His Val Tyr Thr Phe Ala Thr Arg Lys Leu Gln Pro Met Ile Thr Ser
            195                 200                 205

Glu Thr Gly Lys Ala Leu Ile Gln Thr Cys Leu Asn Ser Pro Asp Ser
        210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
                260                 265                 270

Pro Gly Thr Thr Ser Thr Ile Gln Thr Ala Pro Ser Thr Ser Thr Thr
                275                 280                 285

Met Gln Val Ser Ser Gly Pro Ser Phe Pro Ile Thr Asn Tyr Leu Ala
            290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Ser Gly Gly Leu
                325                 330                 335

Met Gln Leu Pro Thr Ser Phe Thr Leu Met Pro Gly Gly Ala Val Ala
                340                 345                 350

Gln Gln Val Pro Val Gln Ala Ile Gln Val His Gln Ala Pro Gln Gln
            355                 360                 365

Ala Ser Pro Ser Arg Asp Ser Ser Thr Asp Leu Thr Gln Thr Ser Ser
        370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
                420                 425                 430

Ala Phe Ser Gln Ala Pro Ser Thr Met Gln Val Ser His Ser Gln Val
            435                 440                 445

Gln Glu Pro Gly Gly Val Pro Gln Val Phe Leu Thr Ala Ser Ser Gly
        450                 455                 460

Thr Val Gln Ile Pro Val Ser Ala Val Gln Leu His Gln Met Ala Val
465                 470                 475                 480
```

-continued

Ile Gly Gln Gln Ala Gly Ser Ser Ser Asn Leu Thr Glu Leu Gln Val
              485                 490                 495

Val Asn Leu Asp Thr Ala His Ser Thr Lys Ser Glu
        500                 505

<210> SEQ ID NO 98
<211> LENGTH: 1636
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 98

| | |
|---|---|
| auggaucccg ggcagcagcc gccgccucaa ccggcccccc agggccaagg gcagccgccu | 60 |
| ucgcagcccc cgcaggggca gggcccgccg uccggacccg ggcaaccggc acccgcggcg | 120 |
| acccaggcgg cgccgcaggc accccccgcc gggcaucaga ucgugcacgu ccgcggggac | 180 |
| ucggagaccg accuggaggc gcucuucaac gccgucauga accccaagac ggccaacgug | 240 |
| ccccagaccg ugcccaugag cuccggaag cugcccguau cccuucuuca agccgccgga | 300 |
| gcccaaaucc cacucccgac aggccaguac ugaugcaggc acugcaggag cccugacucc | 360 |
| cagcauguuc gagcucauuc cucuccagcu ucucugcagu uggagcugu uucuccuggg | 420 |
| auggaucccg ggcagcagcc gccgccucaa ccggcccccc agggccaagg gcagccgccu | 480 |
| ucgcagcccc cgcaggggca gggcccgccg uccggacccg ggcaaccggc acccgcggcg | 540 |
| acacugaccc ccacuggagu agucucuggc ccagcagcua cacccacagc ucagcaucuu | 600 |
| cgacagucuu cuuuugagaa uaccgauga uguaccucug ccagcgguug ggagauggca | 660 |
| aagacaucuu cuggucagag auacuucuua aaucacaucg aucagacaac aacauggcag | 720 |
| gaccccagga aggccaugcu gucccagaug aacgucacag cccccaccag uccaccagug | 780 |
| cagcagaaua ugaugaacuc ggcuucaggu ccucuuccug augauggga acaagccaug | 840 |
| acucaggaug gagaaauuua cuauauaaac cauaagaaca agaccaccuc uuggcuagac | 900 |
| ccaaggcuug accucguuu ugccaugaac cagagaauca gucagagugc ccagugaaa | 960 |
| cagccaccac cccuggcucc ccagagccca cagggaggcg ucaugggugg cagcaacucc | 1020 |
| aaccagcagc aacagaugcg acugcagcaa cugcagaugg agaaggagag gcugcggcug | 1080 |
| aaacagcaag aacugcuucg gcaggcaaug cggaauauca aucccagcac agcaaauucu | 1140 |
| ccaaaauguc aggaguuagc ccugcguagc caguuaccaa cacuggagca ggauggugg | 1200 |
| acucaaaauc cagugucuuc ucccgggaug ucucaggaau ugagaacaau gacgaccaau | 1260 |
| agcucagauc cuuccuuaa caguggcacc uaucacucuc gagaugagag uacagacagu | 1320 |
| gggacuaagc augagcagcu acagugucccc ucgaaccca gaugcuucc ugaacagugu | 1380 |
| ggaugagaug gauacaggug auacuaucaa ccaaagcacc cugcccucac agcagaaccg | 1440 |
| uuucccagac uaccuugaag ccauuccugg gacaaaugug gaccuuggaa cacuggaagg | 1500 |
| agauggaaug aacauagaag gagaggagcu gaugccaagu cugcaggaag cuuugaguuc | 1560 |
| ugacauccuu aaugcauggg agucuguuuu ggcugccacc aagcuagaua agaaagcuu | 1620 |
| ucuuacaugg uuauag | 1636 |